(12) United States Patent
Mateychuk

(10) Patent No.: US 8,219,204 B2
(45) Date of Patent: Jul. 10, 2012

(54) TELEMETRY ANTENNA FOR AN IMPLANTABLE MEDICAL DEVICE

(75) Inventor: Duane N. Mateychuk, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 953 days.

(21) Appl. No.: 12/241,439

(22) Filed: Sep. 30, 2008

(65) Prior Publication Data
US 2010/0082080 A1    Apr. 1, 2010

(51) Int. Cl.
*A61N 1/00* (2006.01)
(52) U.S. Cl. ......... 607/60
(58) Field of Classification Search ........... 607/60, 607/36, 37
See application file for complete search history.

(56) References Cited

U.S. PATENT DOCUMENTS

| | | | |
|---|---|---|---|
| 7,317,946 B2 | 1/2008 | Twetan et al. | |
| 7,427,965 B2 | 9/2008 | Fabrega-Sanchez et al. | |
| 7,554,493 B1 | 6/2009 | Rahman | |
| 2004/0082977 A1 | 4/2004 | Engmark et al. | |
| 2005/0203584 A1 | 9/2005 | Twetan et al. | |
| 2007/0190866 A1 * | 8/2007 | Zart et al. | 439/736 |

OTHER PUBLICATIONS (PCT/US2009/056306) PCT Notification of Transmittal of the International Search Report and the Written Opinion of the International Searching Authority, 8 pages.

* cited by examiner

*Primary Examiner* — Carl H Layno
*Assistant Examiner* — Jeremiah Kimball
(74) *Attorney, Agent, or Firm* — Stephen W. Bauer; Michael J. Ostrom; Evans M. Mburu

(57) ABSTRACT

A telemetry antenna for an implantable medical device includes one or more segments having a non-linear configuration. In some embodiments, the non-linear configuration provides an antenna having a greater antenna length than the linear lengthwise dimension of the antenna structure. In some embodiments, the non-linear configuration includes a plurality of trapezoidal unit structures.

15 Claims, 7 Drawing Sheets

TELEMETRY ANTENNA FOR AN IMPLANTABLE MEDICAL DEVICE

TECHNICAL FIELD

The present disclosure relates generally to medical devices and more particularly to telemetry antennas for an implantable medical device (IMD).

BACKGROUND

A variety of implantable medical devices (IMD's) exist that provide diagnostic or therapeutic capabilities. These IMD's include, for example, cardiac pacemakers, implantable cardioverters/defibrillators (ICD's), and various tissue, organ and nerve stimulators or sensors. IMD's typically include their components within a hermetically sealed enclosure referred to as a "can" or housing. In some IMD's, a connector header or connector block is attached to the housing and allows interconnection with one or more elongated electrical medical leads.

The header is typically molded from of a relatively hard, dielectric, non-conductive polymer such as tecothane having a thickness approximating the housing thickness. The header includes a mounting surface that conforms to and is mechanically affixed against a surface of the housing.

It has become common to provide a communication link between the hermetically enclosed electronic circuitry of the IMD and an external programmer or monitor or other external medical device (EMD) in order to provide for downlink telemetry (DT) transmission of commands from the external device to the IMD and to allow for uplink telemetry (UT) transmission of stored information and/or sensed physiological parameters from the IMD to the EMD.

As the technology has advanced, IMDs have become ever more complex in possible programmable operating modes, menus of available operating parameters, and capabilities of monitoring increasing varieties of physiologic conditions and electrical signals which place ever increasing demands on the programming system. Additionally, the technology advancements have resulted in a reduction in the physical size of most components utilized in IMDs and thus the physical size of the devices—including the housing—has continually decreased as well. Conventionally, the communication link between the IMD and the EMD is by encoded RF transmissions between an IMD RF telemetry antenna and transceiver and an EMD RF telemetry antenna and transceiver. Generally, the antenna is disposed within the header of the IMD. The reduced overall size of the IMD has resulted in restricted space allocations for an IMD RF telemetry antenna.

"Far field" telemetry, or telemetry over distances beyond the near field region for an IMD is desirable. Various proposals have been advanced to provide an IMD with an antenna that facilitates far field telemetry. The proposals include eliminating the ferrite core, wire coil, RF telemetry antenna, utilizing alternative IMD telemetry antennas, and substituting alternative telemetry transmission systems and schemes employing far higher carrier frequencies and more complex signal coding to enhance the telemetry transmission distances to allow telemetry transmission to take place over a matter of meters rather than inches. These approaches are generally undesirable in that depending upon the option selected they require additional components added to the housing, reduce the effectiveness of other components, create a directional requirement, add extraneous exposed components or require additional considerations during implant, or that they are simply infeasible due to space constraints.

To implement effective telemetry from a given IMD over the distances desired, the driving power should be efficiently converted to maximize the far-field component generated by the antenna. One factor affecting the far field component is the length of the antenna with respect to the wavelength of the driving signal. While many types of antennas function according to a variety of parameters, it is generally desirable to provide an antenna having a minimum length equivalent to one-quarter or one-half the wavelength of the driving frequency. However, due to the physical space limitations it has become increasingly difficult to provide a miniaturized antenna that also meets the desired minimum length of one-quarter or one-half the wavelength. Further, as the antenna length decreases the radiation resistance of the antenna diminishes, making it more difficult to couple significant power to the antenna thereby decreasing the performance of the antenna. It remains desirable to provide an IMD telemetry antenna with improved performance.

The disclosure will be best understood from the following description of specific embodiments when read in connection with the accompanying drawings which are illustrative in nature and non-limiting. Various modifications are permissible while remaining within the spirit and scope of the disclosure as provided in the attached claims.

DETAILED DESCRIPTION

The following description provides various embodiments of an IMD telemetry antenna that provides improved RF telemetry in the context of an ICD. However, the antenna may be implemented with a wide variety of IMD's.

Figure 1:
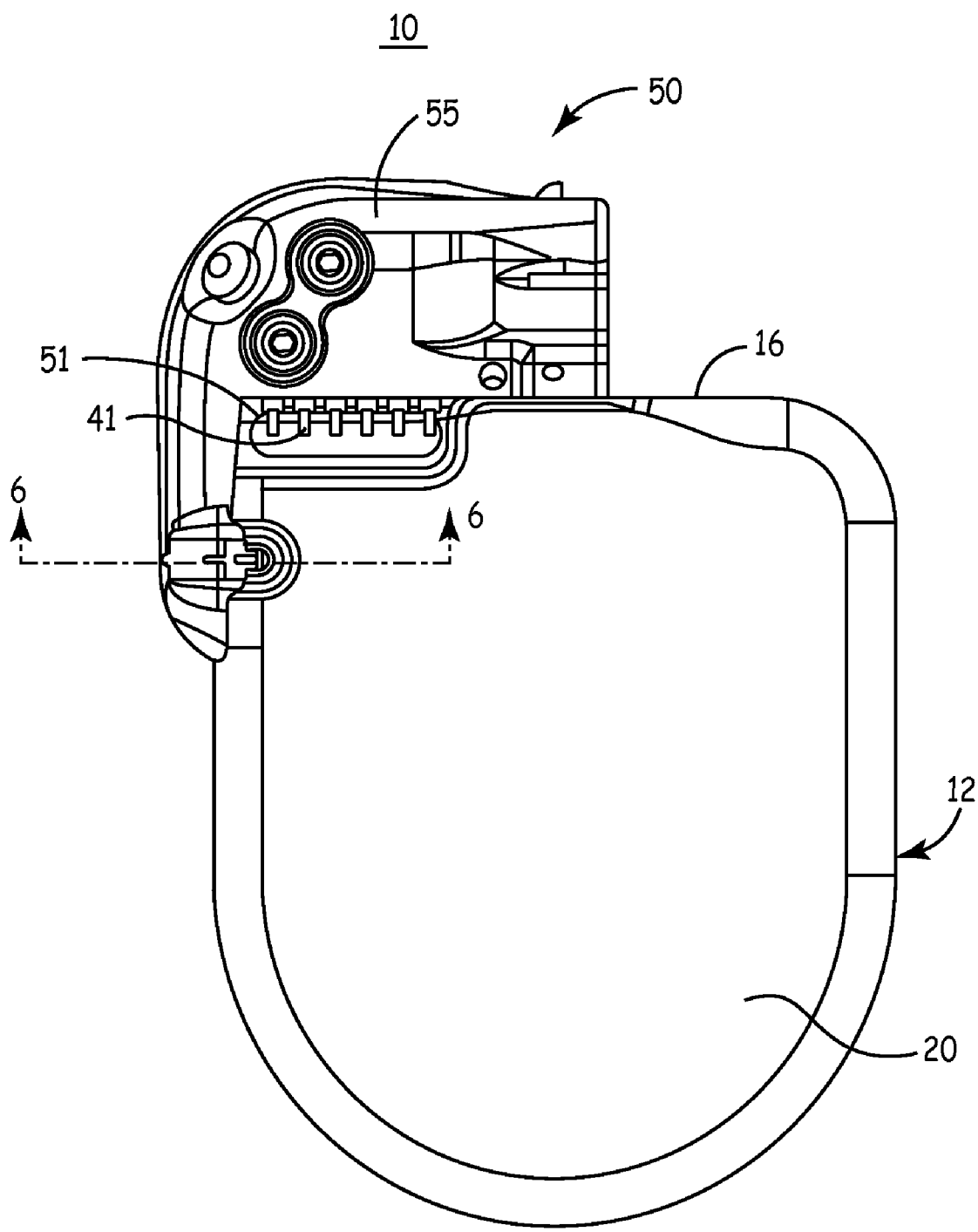
FIG. 1 is a plan view of a first embodiment of an ICD fabricated with an elongated IMD antenna within the connector header in accordance with one embodiment.

FIG. 1 illustrates one embodiment in which ICD 10 includes a connector header 50, hermetically sealed with IMD housing 12. An IMD telemetry antenna 70 (shown in FIG. 4A) is disposed within the connector header 50. In an exemplary embodiment, antenna 70 is a transmission line comprised of a conductive material that forms all or part of a path for directing transmission of energy, such as electromagnetic waves from one place to another. A set of ICD leads having cardioversion/defibrillation electrodes and pace/sense electrodes disposed in operative relation to a patient's heart are adapted to be coupled to the connector header 50 in a manner well known in the art. The ICD 10 is adapted to be implanted subcutaneously in the body of a patient such that the disposed IMD telemetry antenna 70 is encased within body tissue and fluids including epidermal layers, subcutaneous fat layers and/or muscle layers.

The hermetically sealed housing 12 is often manufactured as an assembly or attachment with the separately fabricated connector header 50. In the manufacturing process, electrical connections are made between IC connector pads or terminals with the inner ends of the connector header feedthrough pins 41. An electrical connection is also made between the inner end of the antenna feedthrough pin 33 of antenna feedthrough 30 and the RF telemetry circuitry 39 as described further below in reference to FIG. 5. Each of the connector feedthrough pins 41 are bent over and welded to a respective one of the electrical pads 51.

Figure 2:
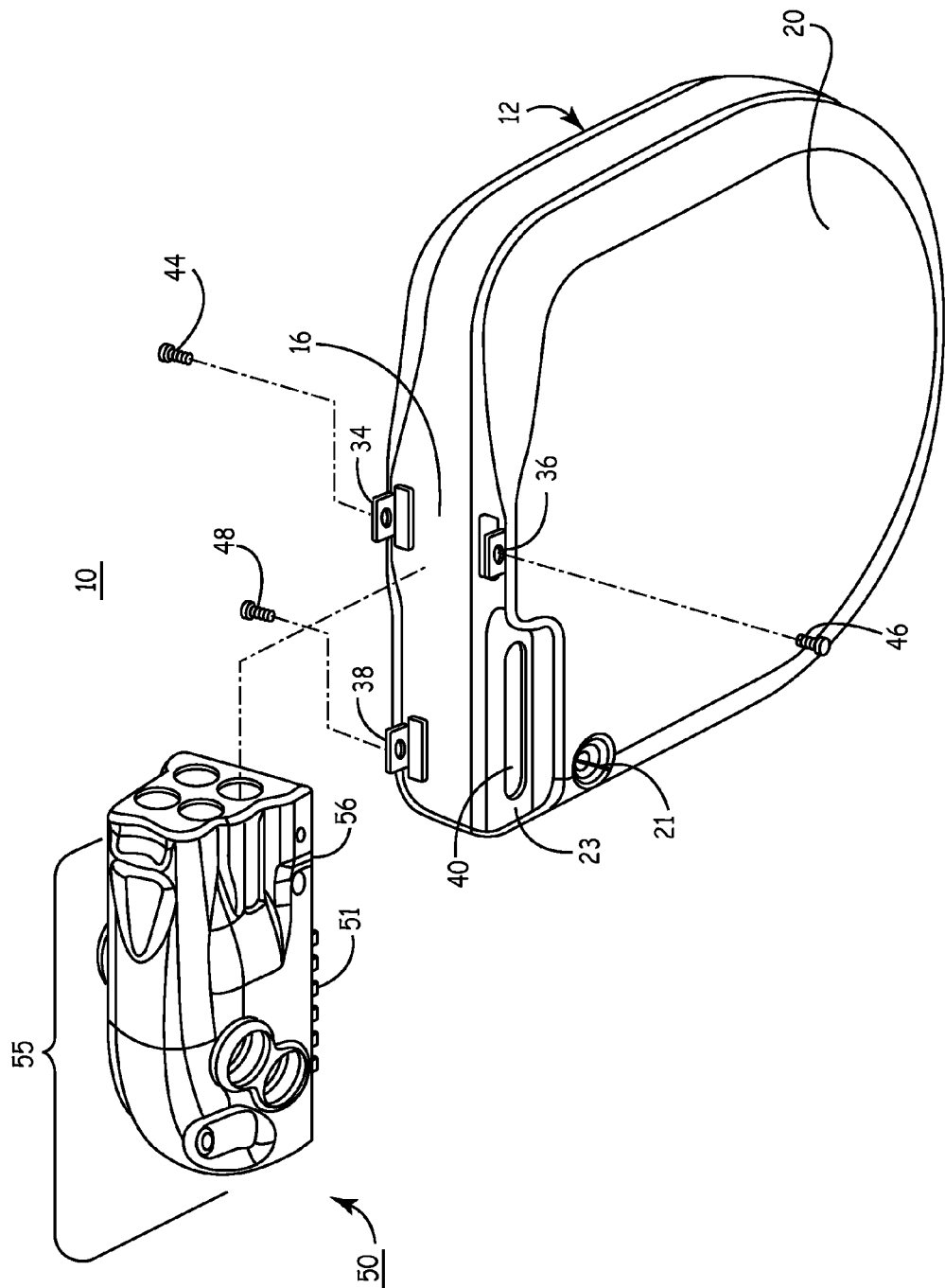
FIG. 2 is an exploded front perspective view of the ICD of FIG. 1 depicting the connector header disposed in relation to the ICD housing.

In the embodiment illustrated in FIG. 2, the connector header 50 is formed as a separate assembly comprising a header segment 55 having a substantially contiguous header segment side 56, which is shaped to fit against a contiguous minor side 16 and to receive connector tabs 34, 36 and 38. A connector recess 23 is formed into the planar major side 20 adjacent to second minor side 16 that includes an elongated feedthrough hole that accommodates a single, elongated, feedthrough 40 supporting a plurality of feedthrough pins 41. The connector header 50 is mechanically fixed to the minor side 16 by use of pins or screws 44, 46, and 48 that fit through aligned holes in connector header 50 and the respective connector tabs 34, 36, and 38. The connector header 50 is also formed with an array of connector header electrical pads 51.

Figure 3:
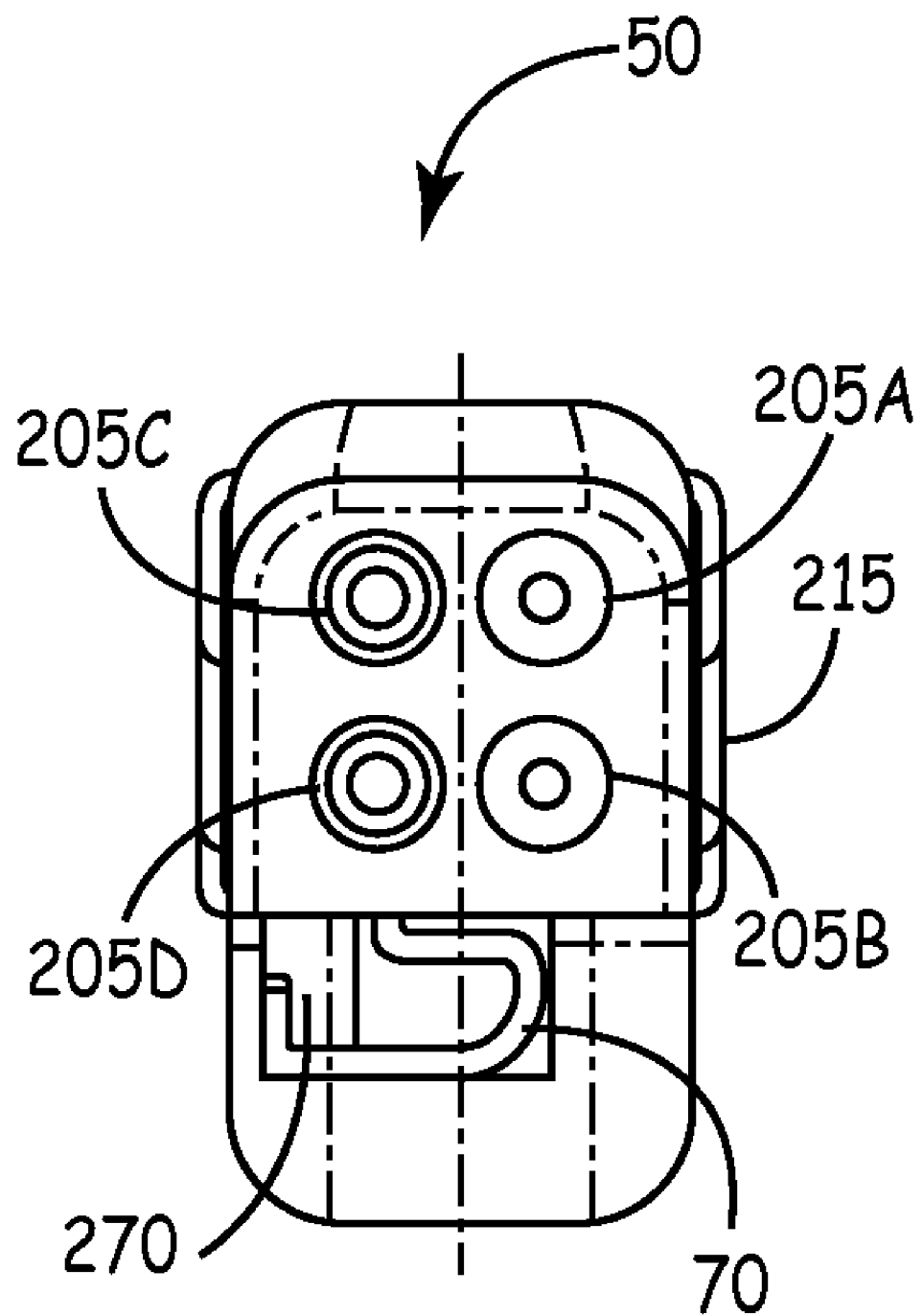
FIG. 3 is a front elevational view of the header and trapezoidal unit structure antenna of FIG. 4A.

FIG. 3 illustrates an interior cross-sectional end view of the header 50 that includes a variety of structural components such as the connectors 205A-D. For a given header 50, these structural elements define the free space available to position the antenna 70. In the illustrated embodiments, a channel 210 (FIG. 4A) is provided proximal to an upper portion of the header 50 and generally positions the antenna 70 over/behind (as illustrated) these components.

Figure 4A:
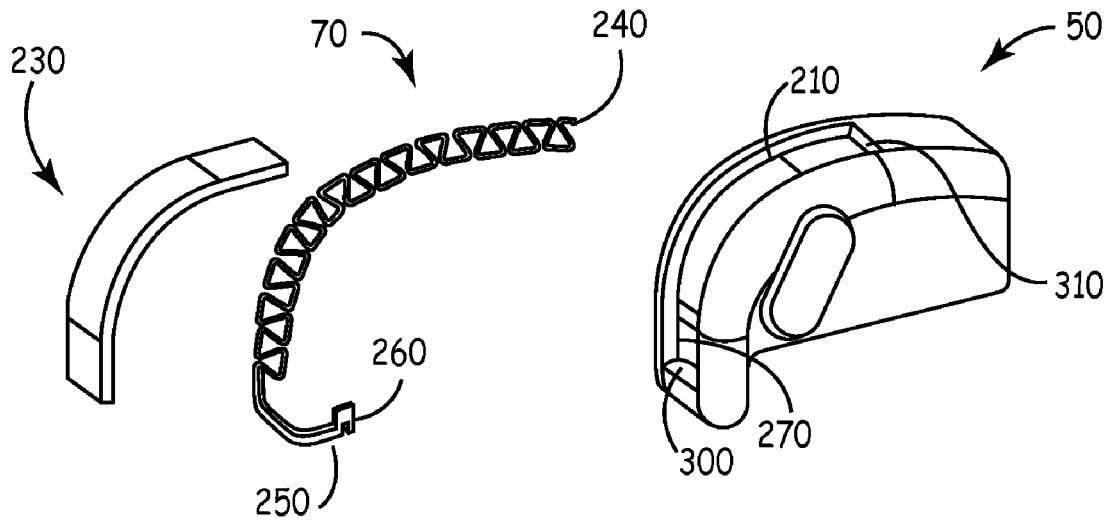
FIG. 4A is an isometric, exploded view of a header assembly and a trapezoidal unit structure antenna.
Figure 4B:
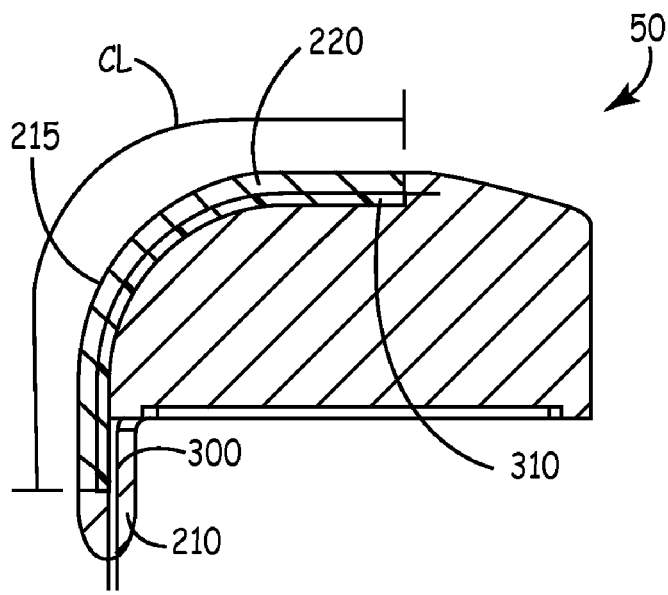
FIG. 4B is a side elevational view of the header and trapezoidal unit structure antenna of FIG. 4A.

Referring to FIG. 4A and 4B the antenna 70 can be positioned anywhere within the header 50 with respect to these various components. Of course, any other components disposed within the header 50 may affect positioning and performance; however, the antenna 70 may be positioned in various orientations and situated anywhere within the volume of the header 50. The header 50 may be designed to accommodate a given antenna 70 or the antenna 70 may be adapted to a preexisting header design.

In addition, the antenna 70 is generally uniformly spaced from an exterior surface 215 of the header 50. As the header 50 is typically made from a dielectric material, the effect of such material on the antenna's properties is relevant. Furthermore, in actual use, the ICD 10 is implanted within human tissue having a relatively high dielectric value. With the illustrated embodiment, the distance from the antenna to exterior surface 215 is uniform and the exterior surface 215 itself is uniform; thus, contact with surrounding body tissue and fluids is even. Hence, the antenna 70 is also uniformly spaced from the header/tissue interface. The distance selected is based upon the specific parameters and performance requirements chosen for the antenna 70 and the transceiver utilized and may be greater or less than those of the exemplary embodiments.

Any number of known molding techniques may be utilized to mold the header 50. As illustrated in FIG. 4A a channel 210 is formed within the header 50. The antenna 70 (not shown) is placed within the channel 210. Once the antenna 70 is positioned within the channel 210, a cover 230 is placed over the channel 210 and sealed. Generally, the cover 230 will hermetically seal the antenna 70 within the channel 210. Various techniques may be employed to seal the cover 230. For example, the cover 230 may be bonded with an adhesive to the main header portion 200 or may be heat-sealed. Alternatively, the main header portion 200 may be subjected to a secondary molding process after the antenna 70 is placed within the channel 210. With this process, the antenna 70 is completely encased and secured within the header 50. A secondary sealing layer may also be molded or otherwise fabricated over some portion of or the entirety of the header 50.

One benefit of positioning the antenna 70 within header 50 in the illustrated orientation is that telemetry performance will not be affected by the orientation of the ICD 10 (FIG. 1) when it is implanted. The ICD 10 will always be implanted such that a major plane of the device 10 projects outward from the patient. Depending upon the implantation site and the preferences of the physician, either major surface may face outward; however, the antenna performance will be the same regardless of which major surface faces outward or the rotational orientation of the device 10.

The antenna 70 includes a proximal end 250 and a distal end 240. When assembled, the majority of the antenna 70 is contained within the header 50. A connector tab 260 depends from the proximal end 250 and projects through an interior opening 270 within the header 50. The connector tab 260 then makes electrical contact with terminals in communication with the telemetry circuitry 39 (FIG. 6) disposed within the housing. This may be accomplished with welding or otherwise bonding the tab 260 to the terminal or the components may be shaped to generate a frictional or clamping arrangement.

As illustrated in FIG. 4B, the channel 210 defines a constraining length CL as the linear path between a proximal end 300 and a distal end 310 of the channel 210 while following the contour of the channel 210. The channel 210 is not limited to the shape, location, and relative length illustrated; however, the channel 210 (or space dedicated to the antenna) ultimately provides for the constraining length CL. Thus the antenna length AL of a substrate 400 (FIG. 5A) of a linear antenna would not exceed the constraining length CL. It is the antenna length AL (FIG. 5A) that is relevant to determining the operability and effectiveness of a given antenna in a given system.

Figure 5A:
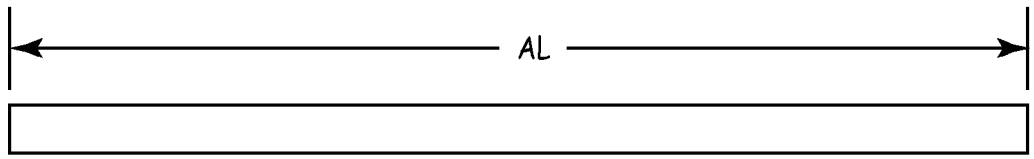
FIG. 5A is a schematic illustration of a linear substrate.

As previously indicated, the antenna length AL affects the far field telemetry. However, due to the continued reduction in size of IMD's, the constraining length CL and the product width PW of the connector header 210 are often insufficient to mount a linear antenna substrate with antenna length AL of at least one-quarter the wavelength of the driving frequency of the ICD 10. To provide an antenna length AL that exceeds the constraining length CL of the channel 210, a linear antenna substrate 400 shown in FIG. 5A is constructed into a non linear antenna configuration. With a non-linear configuration an antenna length AL that is at least one-quarter the wavelength of the driving frequency of the ICD 10 may be attained because the planar lengthwise dimension (i.e., the operative linear distance from the non-linearly configured antenna's distal tip to proximal tip) is equal to or less than the constraining length CL.

A corollary to configuring the linear antenna substrate into a non-linear configuration is that the performance of the resulting antenna is impacted. Table 1 contains definitions of the parameters that are considered in evaluating the performance of antenna 70.

TABLE 1

| Parameters | Definition |
| --- | --- |
| Incident Wave, a | The propagating wave from the RF telemetry circuitry 39 to the antenna 70 |
| Reflected Wave, b | The propagating wave from the antenna 70 to the RF telemetry circuitry 39. |
| Incident Power, $P_{inc}$ | The power from the propagating wave from the RF telemetry circuitry 39 to the antenna 70. |
| Reflected Power, $P_{ref}$ | The power from the propagating wave from the antenna 70 to the RF telemetry circuitry 39. |
| Input Power, $P_{in}$ | The net power going into the antenna 70 ($P_{inc} - P_{ref}$). |
| Radiated Power, $P_{rad}$ | The power radiated into space from the antenna 70. |
| Source Impedance, $Z_s$ | The impedance of the excitation source (RF telemetry circuitry 39) |
| Antenna Impedance, $Z_a$ | The input impedance of the antenna 70. |
| Antenna Efficiency | The ratio between $P_{rad}$ and $P_{inc}$ ($P_{rad}/P_{inc}$). |
| Radiation Efficiency | The ratio between $P_{rad}$ and $P_{in}$ ($P_{rad}/P_{in}$). |

One factor that may be evaluated in determining the performance of an antenna is a conjugate match factor of the antenna 70. The conjugate match factor is the ratio between an antenna's input power $P_{in}$, with a first set of source impedance $Z_s$ and antenna impedance $Z_a$ and the antenna input power $P_{in}$ with a second set of source impedance $Z_s$ and antenna impedance $Z_a$ where the second set assumes antenna impedance $Z_a$ is a conjugate match of source impedance $Z_s$. Conjugate match factors range from zero to one. When the conjugate match factor is one, the antenna impedance $Z_a$ is conjugate matched to the source impedance $Z_s$ and the antenna is fully efficient. Conversely, when the conjugate match factor is zero, the antenna's performance is minimally efficient. Another factor in evaluating the performance of antenna 70 is the radiation efficiency. The radiation efficiency is the ratio between radiated power $P_{rad}$ and the input power $P_{in}$. Similarly, the radiation efficiency spans the range from zero to one with one being the most efficient.

Figure 5B:
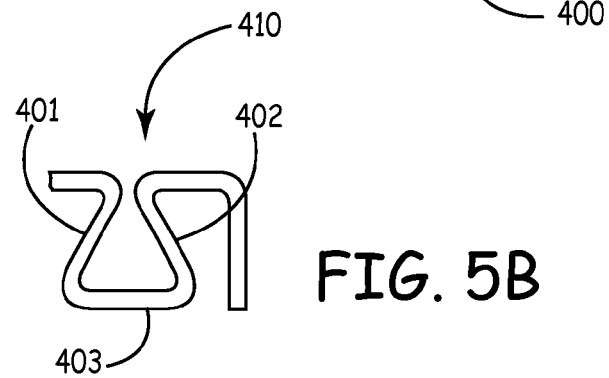
FIG. 5B illustrates a definable portion of the trapezoidal unit structure antenna.

FIG. 5B illustrates one embodiment wherein the antenna substrate 400 (FIG. 5A) is configured into a plurality of trapezoidal unit structures—a configuration that enables the conjugate match factor to approach one. As used herein, the designation "trapezoidal" refers to a three sided structure 410, as shown in FIG. 5B, which is a modification of the commonly known four sided trapezoid geometrical shape. The trapezoidal structure 410 consists of two congruent sides 401, 402 and a bottom side 403 of a trapezoidal geometry shape.

Even with the trapezoidal unit structure configuration, the antenna length AL may be less than one-quarter the wavelength of the driving frequency of the ICD 10. This may arise because the constraining length CL of the channel 210 and the product width PW of the antenna 70 could still restrict the length of the antenna to less than one-quarter the wavelength of the driving frequency. An antenna that is shorter than one-quarter wavelength of the frequency of interest is known as an "electrically short" antenna. Nevertheless, the trapezoidal unit structure configuration of antenna 70 exhibits an increased radiation resistance which increases the antenna impedance $Z_a$ presented which is attributed to the improved efficiency of the antenna 70. In addition, the increased antenna impedance $Z_a$ enables the coupling of significant power to the ICD 10.

Figure 5C:
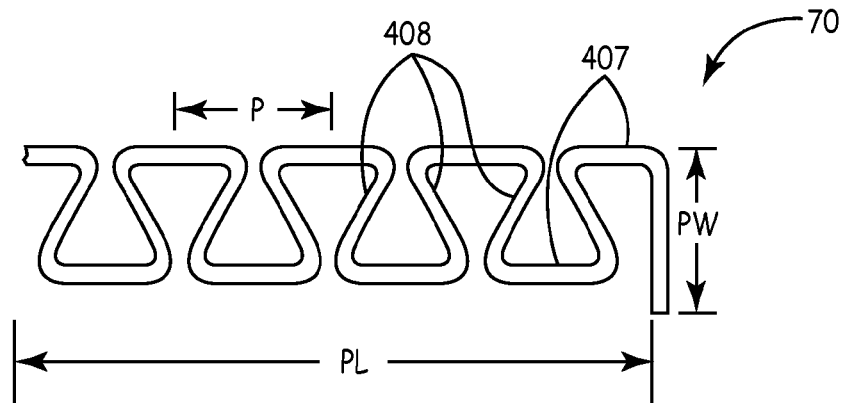
FIG. 5C is a schematic illustration of a trapezoidal unit structure antenna configuration.

FIG. 5C illustrates one embodiment of antenna 70 wherein multiple trapezoidal unit structures are interconnected in an alternating inverted manner. In the embodiment, adjacent congruent sides of the trapezoidal unit structure 410 are coupled to form a common congruent segment 408. The embodiment illustrated in the FIG. 5C is merely exemplary and is not intended to be limiting. For example, rather than forming antenna 70 from multiple trapezoidal unit structures, a linear antenna conductor may be shaped into the illustrated configuration of FIG. 5C.

Although the antenna 70 has the same antenna length AL as the substrate 400, the product length PL of the trapezoidal unit structure antenna 70 is shorter than the antenna length AL. The product length PL is equal to or less than the constraining length CL. The connector header channel must have a width sufficient to receive the antenna 70, having width PW which is defined by the trapezoidal unit structure configuration. Thus the antenna 70 can be accommodated in the header channel 210, illustrated in FIG. 4A, having a constraining length CL that is less than the antenna length AL.

Referring back to FIG. 5C, there are a number of variables that affect the geometry of the antenna 70. Initially, the overall material length or antenna length AL (FIG. 5A) is selected accordingly. The desired product width PW is also determined. Considerations include, for example, the volume of the available space within the header 50. The pitch P is defined as the distance between two subsequent, similar points, e.g., peak to peak as illustrated. The smaller the pitch P, the longer the antenna length AL (FIG. 5A) for a given constraining length CL (FIG. 4B).

Rather than having each of the congruent sides 401, 402 and the bottom side 403 interconnected with arcing junctions, the junctions may be linear to form angled junctions. Typically, the length of the horizontal segment(s) 407 would then be greater than the length of the arc segments. The arc dimensions would then dictate the pitch, assuming the horizontal segments 407 are linear and parallel. The horizontal segments 407 could be linear and non-parallel. In such an embodiment, the offset angle as well as the length of the segment would affect the pitch.

The pitch P can be varied to increase or decrease the product length of the antenna 70. The pitch P does not need to be uniform over the entire antenna 70 and can be varied in any number of ways. For example, linear sections or sections having various curvilinear patterns may be used to position the antenna within the header 50 in the desired configuration.

Figure 6:
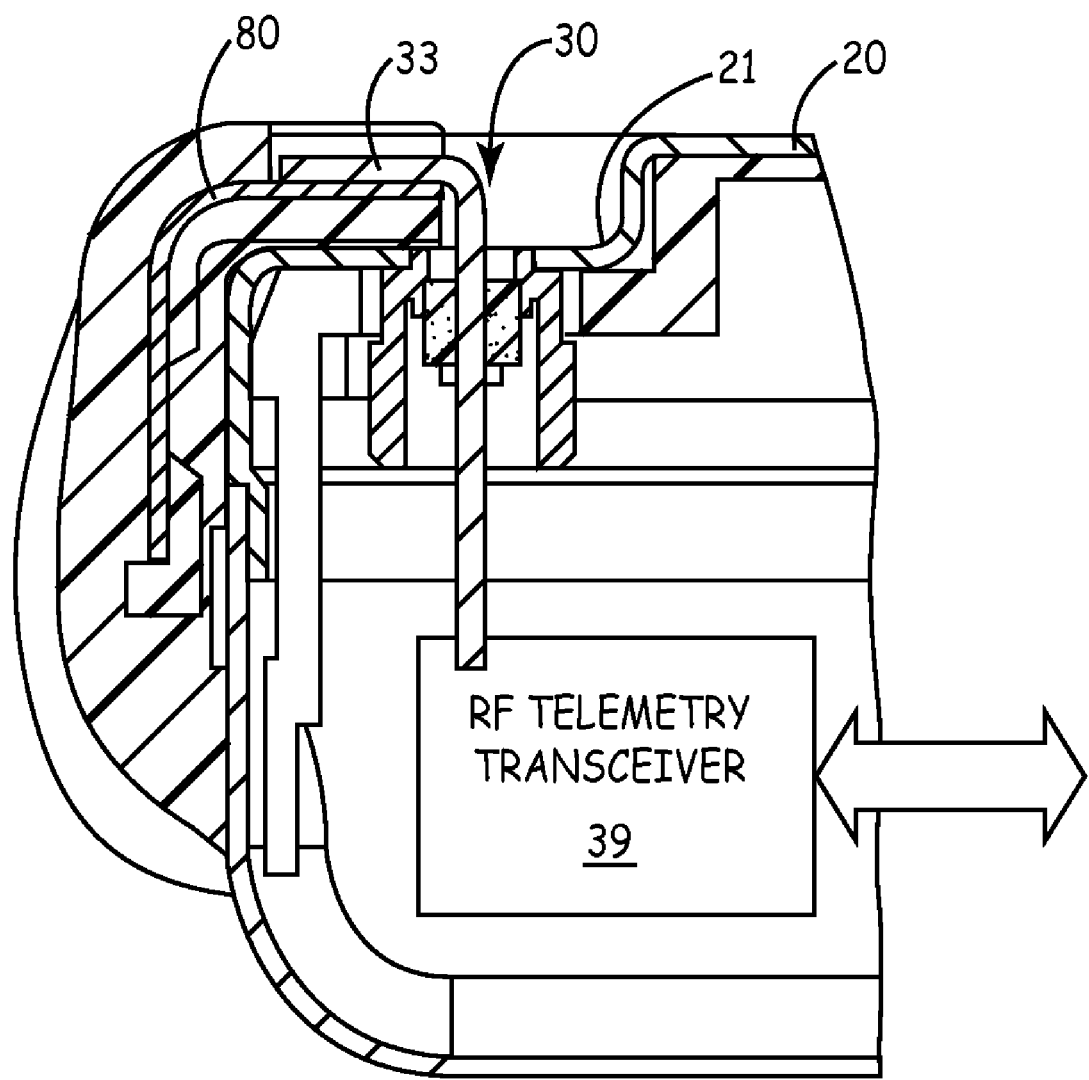
FIG. 6 is an enlarged cross-section view taken along lines 6-6 in FIG. 1 depicting the attachment of the external end of the antenna feedthrough pin to a welding tab of the telemetry antenna wire strip and the internal end of the antenna feedthrough pin to schematically depicted RF telemetry circuitry of the ICD.

As previously discussed, one of the primary functions of the IMD telemetry antenna is to convert UHF signals into electromagnetic power. To provide a complete understanding of antenna 70, a generalized description of the radiation pattern of an antenna will be provided. This description is for illustrative purposes only and is not meant to be limiting. Furthermore, although the description only pertains to the operation of an antenna during transmission, those skilled in the art will recognize that the receiving pattern is identical to the antenna's radiation pattern. Radiation pattern refers to the directional (angular) dependence of radiation from the antenna and include the near field, the radiating near field and far field. The near field is that part of the radiated field nearest to the antenna. The radiating near field is that portion of the near field region of an antenna between the far field and a reactive portion of the near field region, wherein the angular field distribution is dependent upon distance from the antenna. The term reactive portion of the near field arises from the fact that reactive power circulates between the reactive near field and the source, an external matching network, or both. Beyond the near field and the radiated near field is the far field which extends from the region past the largest dimension of the transmitting antenna. In other words, the far field is that region of the field of an antenna where the angular field distribution is essentially independent of the distance from a specified point in the antenna region. Although not intended to be limiting, the antenna 70 is intended to transmit a signal for distances that are much greater than the largest dimension of the transmitting antenna; the radiating pattern being greater than the near field, typically within the radiated near field and the far field. Generally, an antenna's radiated field patterns can be correlated to the antenna's current distributions. Referring to FIG. 6, RF telemetry circuitry 39 provides a UT UHF signal to the antenna, which creates a surface current on the antenna. The antenna far field pattern is determined by the direction of flow of the surface currents on the antenna. The net effect of current flowing along opposite and parallel directions in an antenna is the reduction of the antenna far field due to cancellation.

Figure 5D:
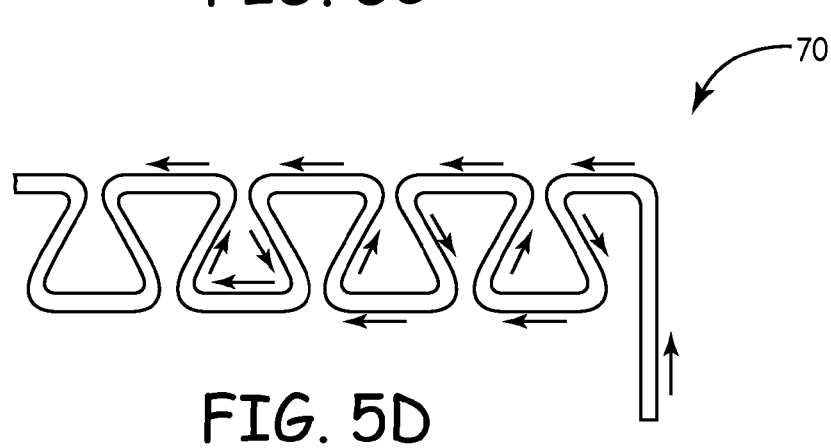
FIG. 5D illustrates an embodiment of a trapezoidal unit structure antenna and illustrating the flow of current in the antenna of FIG. 4C.

FIG. 5D depicts an illustration of the directional flow of the surface current flowing in antenna 70. The surface current flows generally from the proximal end to the distal end of the antenna with the direction of flow being controlled by the configuration of the antenna 70. Surface currents flowing along the congruent sides 401, 402 of the trapezoidal unit structure antenna 70 will be in a generally opposite direction and non-parallel direction to one another. The opposite and non-parallel flow of surface currents results in little to no effect on the antenna's far field pattern.

Turning now to FIG. 6, the electrical coupling associated with antenna 70 is illustrated. The RF telemetry circuitry 39 is electrically connected to the inner end of the antenna feedthrough pin 33. It should be understood that the RF telemetry circuitry 39 is part of the electronics module that controls the operation of the ICD 10 although, for ease of illustration, the entire electronics module has not been shown. RF telemetry circuitry 39 includes an antenna feed line (not shown) which connects the antenna 70 to the transceiver (not shown). The use of the transceiver herein is not intended to be limiting but rather it will be apparent to those skilled in the art that a transmitter or receiver may suitably be substituted without departing from the scope of the teachings. The line transfers radio-frequency energy from the transceiver to antenna 70 and/or from antenna 70 to the transceiver. The connection of the RF telemetry circuitry 39 to the inner end of the antenna feedthrough pin 33 can be made in a variety of ways as by welding the inner end of the antenna feedthrough pin 33 to a substrate pad or clipping the inner end of the antenna feedthrough pin 33 to a cable or flex wire connector extending to a substrate pad or connector. The inner end of the antenna feedthrough pin 33 is electrically coupled to RF telemetry circuitry 39 disposed in close proximity thereto, in a manner that advantageously facilitates impedance matching and reduces losses.

It is desirable that the telemetry circuitry 39 receive the maximum power transmitted from an external source to the antenna 70 and that the antenna 70 transmit the strongest signal propagated from the telemetry circuitry 39. As previously stated, the antenna 70 has an increased radiation resistance which enhances the performance of antenna 70. For efficient transfer of energy, the impedances of antenna 70, the feed line and the transceiver circuitry 39 should be the same. Thus a matching circuit (not shown) coupled to the antenna 70 and the feed line is provided to transform the antenna impedance $Z_a$ to a value close to the impedance of the feed line and the transceiver circuitry.

To further optimize the transfer of power from the RF telemetry circuitry 39 to the antenna 70, the radiation resistance of the antenna 70 should be matched to the characteristic impedance of the matching circuit. The trapezoidal unit structure configuration of antenna 70 improves the input impedance of the antenna because the antenna 70 has a larger real input impedance component and the reactive (imaginary) component is reduced. The larger real input impedance makes it easier to match the antenna 70.

The antenna 70 electrical connection is made between the antenna fixed end at antenna connector pad 80 with the outer end of the antenna feedthrough pin 33 of antenna feedthrough 30 after the antenna connector pad 80 is slipped laterally into the telemetry recess 21 such that the outer extending portion of the feedthrough pin 33 fits into a notch in the leading edge of the antenna connector pad 80 during assembly of the connector header 50 with the hermetically sealed housing 12. The outer extending portion of the feedthrough pin 33 is bent over the exposed outer surface of the antenna connector pad 80 and laser welded thereto in a low profile weld within the telemetry recess 21 formed in the housing major side 20. After testing, the telemetry recess 21 is filled with medical adhesive or epoxy to cover and electrically insulate the bent over, outer extending portion of the feedthrough pin 33 and the exposed outer surface of the antenna connector pad 80.

The impedance of antenna 70 may be matched to the feed line to further optimize the performance of the antenna 70. Matching the impedance of antenna 70 to the feed line eliminates or reduces the reflected power $P_{ref}$. FIGS. 7A-7E illustrate various embodiments of single stub matched antennas. Stub 90 is a shorted or open circuit length of transmission line (such as that used for construction of antenna 70) intended to produce a pure reactance at the attachment point, for the frequency of interest. In other words, the stub 90 takes on reactive properties as a function of its electrical length and thereby facilitates the antenna 70 matching. The illustrations of single stub matching with stub 90 are intended to be an exemplary matching technique, and not limiting. For instance, although the embodiments illustrated in FIGS. 7A-7E are of the open single stub matching variant, short single stub matching, or multiple stub matching may be substituted.

The stub 90 may take the form of any one of several geometry shapes. By way of illustration, but not limitation, the embodiments of FIGS. 7A-7E are of a V-shape, a triangular shape, a check shape, a linear shape, and a curvilinear shape. Of course the stub 90 may also simply be configured into a linear structure. One of the considerations in selecting stub 90 is the directionality of the flow of current propagated from the RF telemetry circuitry 39. Table 2, below, presents the results of various efficiency parameters of antenna 70 containing various geometries of stub 90. Generally, the highest efficiency of antenna 70 is achieved when the direction of flow of current through the stub 90 is non-parallel to the adjacent segments of the trapezoidal unit structures of antenna 70.

TABLE 2

Figure 7A:
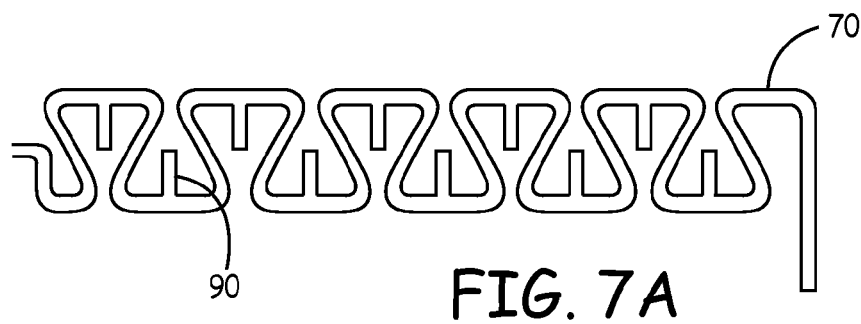
FIGS. 7A-7E illustrate a variety of trapezoidal unit structure antennas having various stub configurations coupled to the antennas.
Figure 7B:
Figure 7C:
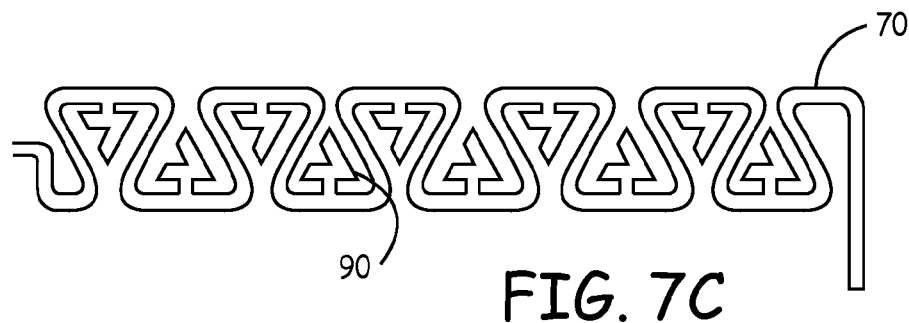
Figure 7D:
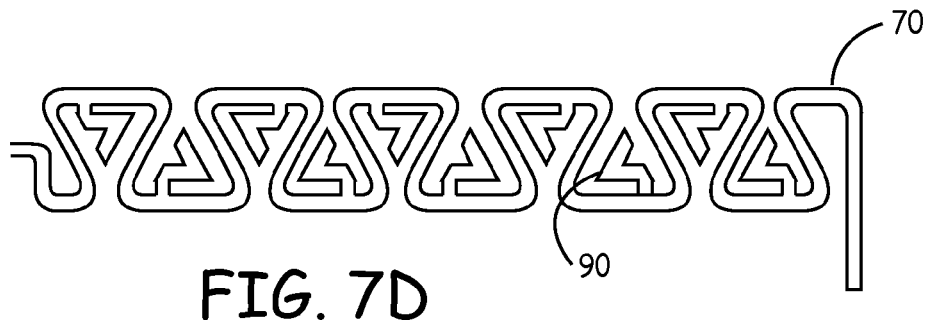
Figure 7E:
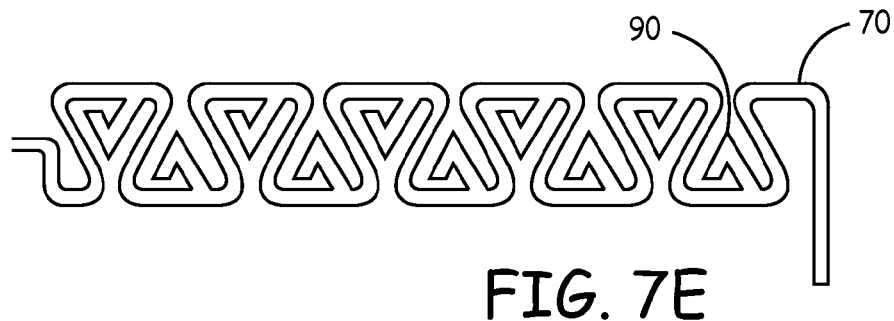

| Antenna | Antenna Footprint (inches) | Antenna Footprint (inches) | Antenna Header Tecothane (mils) | Antenna Metal Length (mils) | Radiation Efficiency (dB) | Matched Efficiency (dB) | Matched Antenna Gain (dB) | Antenna Input Impedance (ohms) |
|---|---|---|---|---|---|---|---|---|
| Antenna Shown in FIG. 7A | 1.122 | 0.164 | 450 | 3851.3 | −27.775819 | −33.796418 | −30.7383 | 14.53 − 1.837E−002i |
| Antenna Shown in FIG. 7B | 1.122 | 0.164 | 450 | 3851.3 | −27.778073 | −33.798673 | −30.7394 | 14.53 + 0.1548i |
| Antenna Shown in FIG. 7C | 1.122 | 0.164 | 450 | 3851.3 | −27.720628 | −33.741228 | −30.7107 | 14.66 + 2.736i |
| Antenna Shown in FIG. 7D | 1.122 | 0.164 | 450 | 3851.3 | −27.717459 | −33.738059 | −30.7091 | 14.66 + 2.696i |
| Antenna Shown in FIG. 7E | 1.122 | 0.164 | 450 | 3851.3 | −27.725848 | −33.746427 | −30.7133 | 14.65 + 2.577i |

The length of the stub 90 is adjusted to alter the wavelength of the antenna in order to achieve a desired reactance value. The reactance of the stub 90 chosen is that which will transform the impedance of antenna 70 into real impedance. In other words, the reactance of the stub 90 is so chosen to cancel out, or minimize the reactive portion of the impedance of antenna 70.

Matching the antenna 70 impedance to the feed line impedance also enhances the radiation efficiency. This is because matching eliminates or reduces the reflected power thus increasing the input power $P_{in}$. Consequently, all the input power $P_{in}$ presented to the antenna is delivered to the RF telemetry circuitry 39.

Returning to FIG. 4A, the antenna 70 is illustrated as a separate component that is coupled with the header 50. Antenna 70 may be fabricated from any appropriate material including conductive metals, and preferably those with high conductivity such as, for example, niobium, titanium and titanium alloys. To fabricate the antenna 70, raw material may be taken from a linear form and bent into the desired configuration. For example, wire having a cylindrical cross section is well suited for such a bending process.

The antenna 70 in the illustrated embodiment utilizes a material having a rectilinear cross section. While not required, such material allows for a difference between the width and thickness of the material. That is, the area of the outwardly radiating surfaces can be increased relative to the area of the lateral edge(s). Furthermore, the material may provide more rigidity and/or structural integrity to the antenna 70. If raw material having a rectilinear cross section is utilized, it too may be bent to fabricate the antenna 70.

Alternatively, the antenna 70 is formed from a stamping process wherein raw material is press formed into the appropriate configuration or by utilizing casting methods that are well known. Photolithography or other etching techniques may be employed and are particularly applicable to small scale, complex patterns. Generally, the antenna 70 is fabricated as a single unitary element; however, welding or other bonding techniques may be utilized to combine multiple components together. For example, connector tab 260 may be a separate element that is coupled with the remainder of the substrate to form a completed antenna 70. Multiple sections may be joined to form an antenna having a given length. Depending upon the fabrication techniques, the design parameters, and material selections, the antenna 70 may be formed into its final configuration during initial manufacture or a multi-step process may be implemented. For example, a linear substrate having the trapezoidal unit structure may first be formed from, e.g., an etching process. That substrate may then be curved (e.g., the side profile illustrated in FIG. 4A) to complement the channel 210. Finally, the connector tab 260 and the relevant dependant portions may be appropriately angled or attached if separate.

In one embodiment, antenna 70 is fabricated from titanium and has a cross sectional thickness of 20 mils and a cross sectional width of 30 mils. In another embodiment, the titanium has a cross sectional thickness of 16 mils and a cross sectional width of the 20 mils. The overall antenna length AL varies from almost zero to any length that may be placed within the volume of the header 200. In certain embodiments, the antenna length is between 0.5 and 10 inches, in other embodiments the antenna length is between 2 to 3 inches, and in other embodiments, the antenna length is approximately 2.75 inches, and in another embodiment, the antenna length is 6.8 inches. As previously discussed, the actual antenna length desired will depend upon various transmission factors such as the frequency of the driving signal.

While certain geometrical configurations have been illustrated, they should not be taken as limiting. Although the embodiments of the antenna 70 have been illustrated as having linear planes, in practice, the antenna can be non-linear in any of its planes to facilitate installation in a non-linear channel 210. Furthermore, more complex geometries employing the illustrated principles may also be incorporated. For example, additional congruent segments could be added to the three sided trapezoidal structure. Additionally, while all the unit structures are illustrated as having segments of uniform length, the unit structures could be designed as being non-uniform or various segments created from non-uniform lengths without departing from the spirit of the present disclosure.

It is therefore to be understood, that within the scope of the appended claims, the disclosure may be practiced otherwise than as specifically described without actually departing from the spirit and scope of the present disclosure.

The invention claimed is:

1. An implanted medical device comprising:
   an electronics module;
   a housing enclosing the electronics module;
   a header coupled with the housing; and
   an antenna disposed within the header, said antenna configured in a plurality of continuous unit structures, said unit structure defining a generally trapezoidal structure having three or more segments, wherein each segment of said unit structure is configured to extend in a direction such that the flow of current propagated from the electronics module through mirroring segments of the unit structure is non-parallel.

2. The implanted medical device of claim 1, wherein the antenna is electrically short.

3. The implanted medical device of claim 1, wherein the segments are generally linear.

4. The implanted medical device of claim 1, wherein the segments are arcuate.

5. The implanted medical device of claim 1, wherein the plurality of continuous unit structures are formed from a unitary antenna material.

6. The implanted medical device of claim 1, wherein the plurality of continuous unit structures are formed from multiple interconnected segments of antenna material.

7. The implanted medical device of claim 6, further comprising arc segments interconnecting the segments.

8. The implanted medical device of claim 6, wherein the antenna material is made of conductive wire.

9. The implanted medical device of claim 1, wherein the three or more segments of the trapezoidal structure define at least two acute angles.

10. An implanted medical device comprising:
    a housing; and
    an antenna located on the surface of the housing, said antenna including:
    a plurality of unit structures having a generally trapezoidal configuration wherein adjacent unit structures share a common segment and are interconnected in an alternating inverted configuration.

11. The implanted medical device of claim 10, wherein the unit structure comprises at least three segments.

12. The implanted medical device of claim 11, wherein a current propagated through adjacent segments of the unit structure flows in a generally non-parallel direction.

13. The implanted medical device of claim 11, wherein the at least three segments define at least two acute angles.

14. The implanted medical device of claim 10, further comprising a stub coupled to at least one segment of the unit structure.

15. The implanted medical device of claim 14, wherein at least a portion of the stub is configured into a geometry selected from the group consisting of a V-shape, a triangular shape, a check shape, a linear shape, a curvilinear shape, and variations thereof.

* * * * *